US008133878B1

(12) United States Patent
Hajjar et al.

(10) Patent No.: US 8,133,878 B1
(45) Date of Patent: *Mar. 13, 2012

(54) METHODS FOR TREATING RESTENOSIS

(75) Inventors: Roger J. Hajjar, Cambridge, MA (US);
Anne-Marie Lompr, Egly (FR);
Larissa Lipskaia, Antony (FR);
Federica del Monte, Boston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/951,721

(22) Filed: Nov. 22, 2010

Related U.S. Application Data

(62) Division of application No. 11/982,883, filed on Nov. 6, 2007, now abandoned, which is a division of application No. 10/933,807, filed on Sep. 3, 2004, now Pat. No. 7,291,604.

(60) Provisional application No. 60/499,705, filed on Sep. 3, 2003.

(51) Int. Cl.
*A61K 31/70* (2006.01)
*A61K 48/00* (2006.01)
*C12N 15/00* (2006.01)

(52) U.S. Cl. .................... 514/44 R; 435/456; 435/320.1

(58) Field of Classification Search .................... None
See application file for complete search history.

(56) References Cited

U.S. PATENT DOCUMENTS

| | | | |
|---|---|---|---|
| 4,522,811 A | 6/1985 | Eppstein et al. | |
| 5,163,952 A | 11/1992 | Froix | |
| 5,223,263 A | 6/1993 | Hostetler et al. | |
| 5,252,348 A | 10/1993 | Schreier et al. | |
| 5,264,618 A | 11/1993 | Feigner et al. | |
| 5,304,121 A | 4/1994 | Sahatjian | |
| 5,328,470 A | 7/1994 | Nabel et al. | |
| 5,459,127 A | 10/1995 | Feigner et al. | |
| 5,674,192 A | 10/1997 | Sahatjian et al. | |
| 5,766,625 A | 6/1998 | Schreier et al. | |
| 5,858,784 A | 1/1999 | Debs et al. | |
| 5,932,299 A | 8/1999 | Katoot | |
| 6,024,918 A | 2/2000 | Hendriks et al. | |
| 6,358,556 B1 | 3/2002 | Ding et al. | |
| 6,379,382 B1 | 4/2002 | Yang | |
| 6,387,124 B1 | 5/2002 | Buscemi et al. | |
| 6,391,052 B2 | 5/2002 | Buirge et al. | |
| 6,409,716 B1 | 6/2002 | Sahatjian et al. | |
| 6,451,594 B1 | 9/2002 | Chien et al. | |
| 6,506,408 B1 | 1/2003 | Palasis | |
| 6,506,437 B1 | 1/2003 | Harish et al. | |
| 6,527,801 B1 | 3/2003 | Dutta | |
| 6,541,116 B2 | 4/2003 | Michal et al. | |
| 6,545,748 B1 | 4/2003 | Trozera | |
| 6,569,194 B1 | 5/2003 | Felton | |
| 6,572,645 B2 | 6/2003 | Leonhardt | |
| 6,596,699 B2 | 7/2003 | Zamora et al. | |
| 6,605,110 B2 | 8/2003 | Harrison | |
| 6,605,114 B1 | 8/2003 | Yan et al. | |
| 6,605,274 B1 | 8/2003 | Dillmann et al. | |
| 7,291,604 B2 * | 11/2007 | Hajjar et al. ................. | 514/44 R |
| 2002/0032167 A1 | 3/2002 | Chien et al. | |
| 2002/0040010 A1 | 4/2002 | Rosenzweig et al. | |
| 2002/0159978 A1 | 10/2002 | Allen | |
| 2003/0073653 A1 | 4/2003 | Bureau et al. | |
| 2003/0100889 A1 | 5/2003 | Duverger et al. | |
| 2003/0144200 A1 | 7/2003 | Baird et al. | |
| 2003/0166593 A1 | 9/2003 | Chien et al. | |
| 2004/0121942 A1 | 6/2004 | Chien et al. | |
| 2005/0095227 A1 | 5/2005 | Rosenzweig et al. | |

FOREIGN PATENT DOCUMENTS

| | | |
|---|---|---|
| EP | 1 319 419 | 6/2003 |
| WO | WO 96/13597 | 5/1996 |
| WO | WO 96/26742 | 9/1996 |
| WO | WO 96/33281 | 10/1996 |
| WO | WO 97/15679 | 5/1997 |
| WO | WO 99/04636 | 2/1999 |
| WO | WO 99/30696 | 6/1999 |
| WO | WO 02/087594 | 11/2002 |
| WO | WO 03/004088 | 1/2003 |
| WO | WO 2004/062618 | 7/2004 |

OTHER PUBLICATIONS

Anderson, "Human gene therapy," *Nature*, 392(Suppl.):25-30 (Apr. 30, 1998).
Anger et al. Circulation 98: 2477-2486 (1998).
Ardehali et al., "direct gene transfer into donor hearts at the time of harvest," *J. Thorac. Cardiovasc. Surg.*, 109(4): 716-720 (Apr. 1995).
Avril et al., "Defining the success of cardiac gene therapy: how can nuclear imaging contribute?" *Eur. J. Nucl. Med. Mot. Imaging*, 30(5):757-771 (May 2003).
Baudet et al., "Effects of Thapsigargin and Cyclopiazonic Acid on Twitch Force and Sarcoplasmic Reticulum $Ca^{2+}$ Content of Rabbit Ventricular Muscle," *Circ. Res.*, 73(5):813-819 (Nov. 1993).
Bernecker et al., "Gene Therapy for the Treatment of Heart Failure—Calcium Signaling," *Semin. Thorac. Cardiovasc. Surg.*, 15(3):268-276 (Jul. 2003).
Boussif et al., "A versatile vector for gene and oligonucleotide transfer into cells in culture and in vivo: Polyethylenimine," *Proc. Natl. Acad. Sci. USA*, 92:7297-7301 (Aug. 1995).
Chaudhri et al., "Contractile effects of adenovirally-mediated increases in SERCA2a activity: A comparison between adult rat and rabbit ventricular myocytes," *Mol. Cell. Biochem,*, 251:103-109 (2003).
Chaudhri et al., "Interaction between increased SERCA2a activity and β-adrenoceptor stimulation in adult rabbit myocytes," *Am. J. Physiol. Heart Circ. Physiol.*, 283:H2450-H2457 (Dec. 2002).
Chen et al., "Gene therapy for brain tumors: Regression of experimental gliomas by adenovirus-mediated gene transfer in vivo," *Proc. Natl, Acad. Sci. USA*, 91:3054-3057 (Apr. 1994).

(Continued)

*Primary Examiner* — Doug Schultz
(74) *Attorney, Agent, or Firm* — Edwards Wildman Palmer LLP; Peter C. Lauro, Esq.; Gabriel J. McCool, Esq.

(57) ABSTRACT

Restenosis in a subject can be treated by administering to a tissue, e.g., a blood vessel, of the subject an agent that increases SERCA activity. For example, a stent that is coated with the agent can be introduced into a blood vessel.

10 Claims, 5 Drawing Sheets

OTHER PUBLICATIONS

Chen et al. Circulation 109: 1898-1903 (2004).
Chu et al., "Cardiomyocyte mechanics in transgenic mice expressing monomeric phospholamban,"*Supplement to Circulation*, 94(8):1-4Z0, Abstract 2449 (Oct. 15, 1996).
Chu et al., "Compensatory Mechanisms Associated With the Hyperdynamic Function of Phospholamban-Deficient Mouse Hearts," *Circ. Res.*, 79(6):1064-1076 (Dec. 1996).
Chu et al., "Isolation of Sarcoplasmic Reticulum Fractions Referable to Longitudinal Tubules and Junctional Terminal Cisternae from Rabbit Skeletal Muscle," *Methods in Enzymology*, 157:36-46 (1988).
Crystal, "*Transfer* of Genes to Humans: Early Lessons and Obstacles to Success," *Science*, 270:404- 410 (Oct. 20, 1995).
Curiel et al., "Gene Transfer to Respiratory Epithelial Cells via the Receptor-mediated Endocytosis Pathway," *Am. J. Respir. Cell Mol. Biol.*, 6(3):247-252 (Mar. 1992).
"CV gene therapy at Genzyme," *Scrip*, No. 2196, p. 18 (Jan. 10, 1997).
Dalesandro et al., "Gene therapy for donor hearts: ex vivo liposome-mediated transfection," J. *Thorac. Cardiovasc. Surg.*, 111(2):416-422 (Feb. 1996).
Davia et al., "Functional alterations in adult rat myocytes after overexpression of phospholamban with use of adenovirus," *Physiol. Genomics*, 1:41-50 (1999).
Davia et al., "SERCA2a Overexpression Decreases the Incidence of After contractions in Adult Rabbit Ventricular Myocytes," *J. Mal. Cell. Cardiol.*, 33:1005-1015 (2001).
del Monte et al., "Efficient Viral Gene Transfer to Rodent Hearts In Vivo," *Methods Mol. Biol.*, 219:179-193 (2003).
del Monte et al., "Improvement in Survival and Cardiac Metabolism After Gene Transfer of Sarcoplasmic Reticulum $Ca^{2+}$-ATPase in a Rat Model of Heart Failure," *Circulation*, 104:1424-1429 (Sep. 18, 2001).
del Monte et al., "Overwhelming Evidence of the Beneficial Effects of SERCA Gene Transfer in Heart Failure," *Circ. Res.*, 88k] 1):E66-E67 (Jun. 8, 2001).
del Monte et al., "Restoration of Contractile Function in Isolated Cardiomyocytes From Failing Human Hearts by Gene Transfer of SERCA2a," *Circulation*, 100:2308-2311 (Dec. 7, 1999).
del Monte et at., "Targeting calcium cycling proteins in heart failure through gene transfer," J. *Physiol.*, 546.1:49-61 (2003).
del Monte et al., "Targeting Phospholamban by Gene Transfer in Human Heart Failure," *Circulation*, 105:904-907 (Feb. 26, 2002).
Deonarain, "Ligand-targeted receptor-mediated vactors for gene delivery," *Exp. Opin. Ther. Patents*, 8(1):53-69 (1998).
Dong et al., "Identification of a cis-Acting Sequence in the Human Plasminogen Activator Inhibitor Type-1 Gene That Mediates Transforming Growth Factor-al Responsiveness in Endothelium in Vivo," *J. Biol. Chem.*, 271(47):29969-29977 (Nov. 22, 1996).
Eastman et al., "A Concentrated and Stable Aerosol Formulation of Cationic Lipid:DNA Complexes Giving High-Level Gene Egression in Mouse Lung," *Hum. Gene Ther.*, 8:765-773 (Apr. 10, 1997).
Ebert et al., "A Moloney MLV-Rat Somatotropin Fusion Gene Produces Biologically Active Somatotropin in a Transgenic Pig," *Mol. Endocrinol.*, 2(3):277-283 (Mar. 1988).
Eizema et al., "Development of possibilities for gene therapy to improve the contractile properties of the failing heart," J. *Mol. Cell. Cardiol.*, 29(5):AI25, Abstract Sa75 (1997).
Feigner et al., "Improved Cationic Lipid Formulations for In Vivo Gene Therapy," *Annals N.Y. Acad. Sci.*, 772:126-139 (1995).
Feigner et al., "Lipofection: A highly efficient, lipid-mediated DNA-transfection procedure," *Proc. Natl. Acad. Sci. USA*, 84:7413-7417 (Nov. 1987).
Fisher et al., "Recombinant adeno-associated virus for muscle directed gene therapy," *Nature Medicine*, 3(3):306-312 (Mar. 1997).
French et al., "Direct In Vivo Gene Transfer Into Porcine Myocardium Using Replication-Deficient Adenovirul Vectors," *Circulation*, 90(5):2414-2424 (Nov. 1994).
Fromes et al., "Gene delivery to the myocardium by intrapericardial injection," *Gene Ther.*, 6:683- 688 (1999).
Fujii et al., "Structure of the Rabbit Phospholamban Gene, Cloning of the Human cDNA, and Assignment of the Gene to Human Chromosome 6," *J. Biol. Chem.*, 266(18):11669-11675 (Jun. 25, 1991).
Genbank Accession No. NP 001672, "ATPase, Ca++ transporting, cardiac muscle, slow twitch 2 isoform 2 [Homo sapiens]".
Genbank Accession No. NP 733765, "ATPase, Ca++ transporting, cardiac muscle, slow twitch 2 isoform 1 [Homo sapiens]".
Genbank Accession No. P16615, "Sarcoplasmic/endoplasmic reticulum calcium ATPase 2 (Calcium pump 2) (SERCA2) (SR Ca(2+) -ATPase 2) (Calcium-transporting ATPase sarcoplasmic reticulum type, slow twitch skeletal muscle isoform) (Endoplasmic reticulum class 1/2 Ca(2+) ATPase)".
Gnatenko et al., "Characterization *of* Recombinant Adeno-Associated Virus-2 as a Vehicle for *Gene* Delivery and Expression into Vascular Cells," *J. Investig. Med.*, 45(2):87-98 (Feb. 1997).
Grupp et al., "The Contribution of Phospholamban, a Sarcoplasmic Reticulum Phosphoprotein, to Myocardial Contractility in Health and Disease," *Heart Failure*, pp. 48- 61 (Apr./May 1995).
Guzman et al., "Efficient Gene Transfer Into Myocardium by Direct Injection of Adenovirus Vectors," *Circ. Res.*, 73(6):1202-1207 (Dec. 1993).
Haghighi et al., "Phospholamban gene expression in cells and transgenic mice,"*Biophysical Journal, Programs and Abstracts, 41st Annual Meeting*, p. A172, Abstract Tu-Pos193 (Mar. 2-6, 1997).
Hajjar, "The promise of gene therapy as a therapeutic modality in heart failure," *Lebanese Medical Journal*, 48(2):86-88 (Mar./Apr. 2000).
Hajjar et al., "Adenoviral Gene Transfer of Phospholamban in Isolated Rat Cardiomyocytes," *Circ. Res.*, 8I(2):145-153 (Aug. 1997).
Hajjar et al., "Effects of Adenoviral Gene Transfer of Phospholamban on Intracellular Calcium Homeostasis in Isolated Myocytes,"*Supplement to Circulation*, 94(8):I-159, Abstract 0922 (Oct. 15, 1996).
Hajjar et al., "Modulation of ventricular function through gene transfer in vivo," *Proc. Natl. Acad. Sci. USA*, 95:5251-5256 (Apr. 1998).
Hajjar et al., "Physiological Effects of Adenoviral Gene Transfer of Sarcoplasmic Reticulum Calcium ATPase in Isolated Rat Myocytes," *Circulation*, 95(2):423-429 (Jan. 21, 1997).
Hajjar et al., "Prospects for Gene Therapy for Heart Failure," *Circ. Res.*, 86:616-621 (Mar. 31, 2000).
Haq et al., "Glycogen Synthase Kinase-3β Is a Negative Regulator of Cardiomyocyte Hypertrophy,"*J. Cell. Biol.*, 151(1):117-129 (Oct. 2, 2000).
Harigaya et al., "Rate of Calcium Binding and Uptake in Normal Animal and Failing Human Cardiac Muscle," *Circ. Res,*, 25:781-794 (Dec. 1969).
Harrer et al., "Expression of phospholamban in C2C12 cells and regulation of endogenous SERCA1 activity," *Mol. Cell. Biochem.*, 146:13-21 (1995).
He et al., "Overexpression of the Rat Sarcoplasmic Reticulum $Ca^{2+}$ ATPase Gene in the Heart of Transgenic Mice Accelerates Calcium Transients and Cardiac Relaxation,"*J. Clin. Invest.*, 100(2):380-389 (Jul. 1997).
Hoit et al., "Echocardiographic Assessment of Left Ventricular Systolic Function in Transgenic *Mice* With Cardiac Specific Over-Expression of Phospholamban," *Journal of the American College of Cardiology*, 27(2;Suppl. A):50A, Abstract 709-1 (Feb. 1996).
Hoit et al., "Influence of Transgenic Overexpression of Phospholamban on Postextrasystolic Potentiation," J. *Mol. Cell. Cardiol.*, 31:2007-2015 (1999).
Huq et al., "Modulating Signaling Pathways in Hypertrophy and Heart Failure by Gene Transfer," J. *Card. Fail.*, 8(6 Suppl):S389-S400 (2002).
Ike et al., "Solid phase synthesis of polynucleotides. VIII. Synthesis of mixed oligodeoxyribonucleotides by the phosphotriester solid phase method," *Nucleic Acids Research*, 11(2):477-488 (1983).
Johnson et al., "Efficiency of gene transfer for restoration of normal airway epithelial function in cystic fibrosis," *Nat. Genet.*, 2:21-25 (Sep. 1992).
Kadambi et al., "Cardiac-specific Overexpression of Phospholamban Alters Calcium Kinetics and Resultant Cardiomyocyte Mechanics in Transgenic Mice,"*J. Clin. Invest.*, 97(2):533-539 (Jan. 1996).
Kadambi et al., "Overexpression of Phospholamban in the Mouse Results in Prolongation of $Ca^{1+}$ Transients and Depressed Contractility in Isolated Cardiomyocytes," *Circulation*, vol. 94, No. 8, Abstract 2894 (1996).

Kang et al., "Free, long-chain, polyunsaturated fatty acids reduce membrane electrical excitability in neonatal rat cardiac myocytes," *Proc. Natl. Acad. Sci. USA*, 92:3997-4001 (Apr. 1995).

Kang et al., "Protective effects of free polyunsaturated fatty acids or arrhythmias induced by lysophosphatidylcholine or palmitoylcarnitine in neonatal rat cardiac myocytes," *European Journal of Pharmacology*, 297:97-106(1996).

Kaplitt et al., "Long-Term Gene Transfer in Porcine Myocardium After Coronary Infusion of an Adeno-Associated Virus Vector," *Ann. Thorac. Surg.*, 62(6):1669-1676 (Dec. 1996).

Kaprielian et al., "Targeting $Ca^{2+}$ cycling proteins and the action potential in heart failure by gene transfer," *Basic Res. Cardiol.*, 97(Suppl. 1):1136-1145 (2002).

Kimura et al., "Phospholamban Regulates the $Ca^{2+}$-ATPase through Intramembrane Interactions," *J. Biol. Chem.*, 271(36):21726-21731 (Sep. 6, 1996).

Kiss et al., "Differential Changes in Cardiac Phospholamban and Sarcoplasmic Reticular $Ca^{2+}$-ATPase Protein Levels. Effects on $Ca^{\prime+}$ Transport and Mechanics in Compensated Pressure—Overload Hypertrophy and Congestive Heart Failure," *Circ. Res.*, 77(4):759-764 (Oct. 1995).

Koban et al., "Regulation of phospholamban and SERCA2a mRNA expression in vivo and in vitro," *Archives of Pharmacology*, 353(Suppl.):R15, Abstract 30 (1996).

Koch et al., "Transgenic Manipulation of Myocardial G Protein-Coupled Receptors and Receptor Kinases," *Circ. Res.*, 78(4):511-516 (Apr. 1996).

Koss et al., "Differential expression of phospholamban gene transcripts in murine atrium and ventricle," *Biophysical Journal, Abstracts, 38th Annual Meeting*, p. A372, Abstract Th-Pos78 (Mar. 6-10, 1994).

Koss et al., "Differential Phospholamban Gene Expression in Murine Cardiac Compartments. Molecular and Physiological Analyses," *Circ. Res.*, 77(2):342-353 (Aug. 1995).

Koss et al., "Phospholamban: A Prominent Regulator of Myocardial Contractility," *Circ. Res.*, 79(6):1059-1063 (Dec. 1996).

Koss et al., "The relative phospholamban and SERCA2 ratio: a critical determinant of myocardial contractility," *Basic Res. Cardiol.*, 92(Suppl. 1):17-24 (1997).

Lalli et al., "Targeted Ablation of the Phospholamban Gene Is Associated With a Marked Decrease in Sensitivity in Aortic Smooth Muscle," *Circ. Res.*, 80(4):506-513 (Apr. 1997).

Lee et al., "Cardiac gene transfer by intracoronary infusion of adenovirus vector-mediated reporter gene in the transplanted mouse heart,". *J. Thorac. Cardiovasc, Surg.*, 111(1):246- 252 (Jan. 1996).

Lefkowitz et al., "Prospects for Cardiovascular Research," *JAMA*, 285(5):581-587 (Feb. 7, 2001).

Lewandowski et al., "Cardiac responses to induced lactate oxidation: NMR analysis of metabolic equilibria," *Am. J. Physiol.*, 269(*Heart. Circ. Physiol.*, 38):H160-H168 (1995).

Li et al., "Calcium transport in phospholamban knockout mouse: relaxation and endogenous CaMKII effects," *Biophysical Journal, Programs and Abstracts, 41st Annual Meeting*, p. A234, Abstract W-AM-16 (Mar. 2-6, 1997).

Liao et al., "$Ca^{2+}$; in Human Heart Failure: A Review and Discussion of Current Areas of Controversy," *Yale J. Biol. Med.*, 67:247-264 (1994).

Lim et al., "Calcineurin and human heart failure," *Nature Medicine*, 5(3):246-247 (Mar. 1999).

Lipskaia et al., "Sarco/Endoplasmic Reticulum $Ca^{2+}$-ATPase Gene Transfer Reduces Vascular Smooth Muscle Cell Proliferation and Neointima Formation in the Rat," *Circ. Res.*, 97:488-495 (Sep. 2, 2005).

Lompre, Poster Presentation, Strasbourg, France, Jun. 21-24, 2003.

Luo et al., "Phospholamban Gene Dosage Effects in the Mammalian Heart," *Circ. Res.*, 78(5):839-847 (May 1996).

Luo et al., "Rapamycin Resistance Tied to Defective Regulation of $p27^{Kip1}$," *Mol. Cell. Biol.*, 16(12):6744-6751 (Dec. 1996).

Luo et al., "Re-introduction of wild-type and mutant phospholamban into phospholamban-deficient hearts reverses enhanced cardiac contractility," *Supplement to Circulation*, 94(8):I-310, Abstract 1807 (Oct. 15, 1996).

Lytton et al., "Molecular Cloning of cDNAs from Human Kidney Coding for Two Alternatively Spliced Products of the Cardiac $Ca^{2+}$-ATPase Gene," *J. Biol. Chem.*, 263(29):15024-15031 (Oct. 15, 1988).

MacNeill et al., "Targeting Signaling Pathways in Heart Failure by Gene Transfer," *Curr. Atheroscler. Rep.*, 5:178-185 (2003).

Maeda et al., "Efficient Gene Transfer into Cardiac Myocytes Using Adeno-Associated Virus (AAV) Vectors," *J. Mol. Cell. Cardiol.*, 30:1341-1348 (1998).

Masaki et al., "Phospholamban deficiency alters inactivation kinetics of L-type Ca2+ chanels in mouse ventricular myocytes," *Am. J. Physiol.*, 272(2):H606-H612 (Feb. 1997).

Maurice et at., "Enhancement of cardiac function after adenoviral-mediated in vivo intracoronary β2-adrenergic receptor gene delivery," *J. Clin. Invest.*, I04(1):21-29 (Jul. 1999) .

McKenzie et al., "Comparative gene transfer efficiency of low molecular weight polylysine DNA-condensing peptides," J. *Peptide Res.*, 54:311-318 (1999).

Metules, "Cardiac gene therapy: The future is now," *RN*, 64(8):54-60 (Aug. 2001).

Miller et al., "Targeted vectors for gene therapy," *FASEB J.*, 9:190-199 (Feb. 1995).

Miyamoto et al., "Adenoviral gene transfer of SERCA2a improves left-ventricular function in aortic- banded rats in transition to heart failure," *Proc. Natl. Acad. Sci. USA*, 97(2):793798 (Jan. 2000).

Morice et al., "A randomized comparison of a sirolimus-eluting stent with a standard stent for coronary revascularization," *N. Engl. J. Med.*, 346(23):1773-1780 (Jun. 6, 2002).

Neubauer et al., "Myocardial Phosphocreatine-to-ATP Ratio Is a Predictor of Mortality in Patients With Dilated Cardiornyopathy,"*Circulation*, 96(7):2190-2.196 (Oct. 7, 1997).

Neumann et al., "Targeted Overexpression of Phospholamban to Mouse Atrium Depresses $Ca^{2+}$ Transport and Contractility," *J. Mel. Cell. Cardiol.*, 30:1991-2002 (1998).

Nuss et al., "Reversal of potassium channel deficiency in cells from failing hearts by adenoviral gene transfer: a prototype for gene therapy for disorders of cardiac excitability and contractility," *Gene Therapy*, 3:900-912 (1996).

O'Connor et al., "Continuous intravenous dobutamine is associated with an increased risk of death in patients with advanced heart failure: Insights from the Flolan International Randomized Survival Trial (FIRST)," *Ain. Heart J.*, 138(1 Pt. 1):78-86 (Jul. 1999).

O'Donnell Circulation research 88: 415-421 (2001).

Pellegrini et al., "Systematic evaluation of distribution of transgene expression after *adenovirus*-mediated gene transfer to the transplanted heart," *Transpl. Int.*, 11:373-377 (1998).

Periasamy Circulation Research 88: 373-375 (2001).

Reddy et al., "Purified, Reconstituted Cardiac $Ca^{2+}$-ATPase Is Regulated by Phospholamban but Not by Direct Phosphorylation with $Ca^{2+}$/Calmodulin-dependent Protein Kinase," *J. Biol. Chem.*, 271(25):14964-14970 (Jun. 21, 1996).

Rothmann et al., "Heart muscle-specific gene expression using replication defective recombinant adenovirus," *Gene Ther.*, 3(10):919-926 (Oct. 1996).

Sawa et al., "Efficiency of in Vivo Gene Transfection Into Transplanted Rat Heart by Coronary Infusion of HVJ Liposome," *Circ.*, 92(9 Suppl. II):II-479-II-482 (Nov. 1, 1995).

Schmidt et al., "Human heart failure: cAMP stimulation of SR $Ca^{2+}$-ATPase activity and phosphorylation level of phospholamban," *Am. J. Physiol,*, 277(Heart Circ. Physiol. 46):H474-H480 (1999).

Shah et al., "In Vivo Ventricular Gene Delivery of a β-Adrenergic Receptor Kinase Inhibitor to the Failing Heart Reverses Cardiac Dysfunction," *Circulation*, 103:1311-1316 (Mar. 6, 2001).

Sinnaeve et al., "Overexpression of a Constitutively Active Protein Kinase G Mutant Reduces Neointima Formation and In-Stent Restenosis," *Circulation*, 105:2911-2916 (Jun. 18, 2002).

Stevenson, "Inotropic Therapy for Heart Failure," *N. Engl. J. Med.*, 339(23):1848-1850 (Dec. 3, 1998).

Strauss et al., "Effects of myosin kinase inhibiting peptide on contractility and $LC_{20}$ phosphorylation in skinned smooth muscle," *Am. J Physiol.*, 262(*Cell Physiol.*, 31):C1437-C1445 (1992).

Sutliff et at, "Phospholamban gene abalation is associated with alterations in portal vein contractility," *FASEB Journal*, 11(3):A215, Abstract 1246 (Feb. 28, 1997).

Svensson et al., "Efficient and Stable Transduction of Cardiomyocytes After Intramyocardial Injection or Intracoronary Perfusion With Recombinant Adeno-Associated Virus Vectors," *Circulation*, 99:201-205 (Jan. 19, 1999).

Terracciano et al., "Overexpression of SERCA2a accelerates repolarisation in rabbit ventricular myocytes," *Cell Calcium*, 31(6):299-305 (2002).

Thomas et al. Nature Rev./Genet. 4: 346-358 (3002).

Thierry et al., "Characterization of liposome-mediated gene delivery: expression, stability and pharmacokinetics of plasmid DNA," *Gene Ther.*, 4(3):226-237 (Mar. 1997).

Tian et al., "Thermodynamic limitation for $Ca^{2+}$ handling contributes to decreased contractile reserve in rat hearts," *Am. J. Physiol.*, 275(*Heart Circ. Physiol.*, 44):H2064-H2071 (1998).

Trapnell et al., "Gene therapy using adenoviral vectors," *Curr. Opin. Biotechnol,*, 5(6):617-625 (Dec. 1994).

Verma et al., "Gene therapy—promises, problems and prospects," *Nature*, 389:239-242 (Sep. 18, 1997).

Wall, "Transgenic Livestock: Progress and Prospects for the Future," *Theriogenology*, 45:57-68 (1996).

Wientzek et al., "Isolation and Characterization of Purified Sarcoplasmic Reticulum Membranes from Isolated Adult Rat Ventricular Myocytes," *J. Mol. Cell. Cardiol.*, 23(10):1149-1163 (Oct. 1991) (Erratum in J *Mot. Cell. Cardiol.*, 23(12):1483 (Dec. 1991)).

Wilson et al. Adv. Drug Deliv. rev. 46: 205-209 (2001).

Xiao et al., "Efficient Long-Term Gene Transfer into Muscle Tissue of Immunocompetent Mice by Adeno-Associated Virus Vector," *Journal of Virology*, 70(11):8098-8108 (Nov. 1996).

Teucher, N., et al., "Excessive Sarcoplasmic/Endoplasmic Reticulum Ca2+-ATPase Expression Causes Increased Sarcoplasmic Reticulum Ca 2+ Uptake But Decreases Myocyte Shortening", Jnl of AHA, Circulation 2004; 110; 3553-3559.

Schmidt, U., et al., "Restoration of Diastolic Function in Senescent Rat Hearts Through Adenoviral Gene Transfer of Sarcoplasmic Reticulum $Ca^{2+}$-ATPase", Circulation, 2000, 101:790-796.

Schwinger, R.H.G., et al, "Unchanged Protein Levels of SERCA II and Phospholamban But Reduced $Ca^{2+}$ Uptake and $Ca^{2+}$-ATPase Activity of Cardiac Sarcoplasmic Reticulum From Dilated Cardiomyopathy Patients Compared With Patients With Nonfailing Hearts", Circulation, 1995; 92; 11; 3220-3228.

Hoshijima, M., "Gene Therapy Targeted at Calcium Handling as an Approach to The Treatment of Heart Failure", Pharmacology & Therapeutics, 2005; 105; 211-228.

Del Monte, F., et al., "Novel Technique of Aortic Banding Followed by Gene Transfer During Hypertrophy and Heart Failure", American Physiological Society, Physiol Genomics, 2002; 9; 49-56.

Goodman and Gilman's "The Pharmacological Basis of Threapeutics", McGraw-Hill, New York, 1996; 77-101.

Baartscheer, A., "Adenovirus Gene Transfer of SERCA in Heart Failure. A Promising Therapeutic Approach?", Cardiovascular Research, 2001, 49; 249-252.

Ahlers, B.A., et al., "Effects of Sarcoplasmic Reticulum Ca2+-ATPase Overexpression in Postinfarction Rat Myocytes", Journal of Applied Physiology, 2005; 98; 2169-2176.

Wang, Y., et al., "Return of Calcium: Manipulating Intracellular Calcium to Prevent Cardiac Pathologies", Proceedings National Acadmy Science, 2004; 101; 16;; 5697-5698.

\* cited by examiner

\* - $p < 0.05$;    \*\* - $p < 0.001$

METHODS FOR TREATING RESTENOSIS

CROSS-REFERENCE TO RELATED APPLICATIONS

This application is a division of U.S. application Ser. No. 11/982,883, filed Nov. 6, 2007, abandoned, which is a division of U.S. application Ser. No. 10/933,807, filed Sep. 3, 2004, now issued as U.S. Pat. No. 7,291,604, which claims priority to U.S. provisional application Ser. No. 610/499,705, filed Sep. 3, 2003. The entire contents of the aforementioned patent applications are hereby incorporated by reference herein in their entireties.

BACKGROUND

Coronary artery disease (CAD) is the leading cause of mortality and morbidity in the developed world. CAD is widely treated by implantation of stents (e.g., balloon stents) in the coronary artery. In-stent restenosis, the recurrence of constriction of an artery following efforts to dilate it, is a common side effect, affecting 20% to 40% of patients by 6 months after percutaneous coronary interventions (PCI), with neointimal hyperplasia being the primary cause.

Rapamycin (sirolimus), an antibiotic that inhibits cell migration and proliferation, is effective in reducing restenosis. However, prolonged exposure of smooth muscle cells to rapamycin results in the development of resistance to the drug (Luo et al., 1996, Mol. Cell. Biol. 16: 6744-6751).

SUMMARY

We have discovered, inter alia, that expression (e.g., overexpression) of sarcoplasmic reticulum (SR) $Ca^{2+}$ ATPase (SERCA) inhibits vascular smooth muscle cell (VSMC) proliferation in vitro and reduces restenosis in vivo.

Accordingly, in one aspect, the disclosure features a method of treating restenosis in a subject, e.g., a human. The method includes: (a) identifying a subject in need of treatment for restenosis (e.g., a subject who has had angioplasty, or a subject who has had a stent placed in a body cavity, such as a blood vessel); and administering to a tissue, e.g., a blood vessel, of the subject an agent that increases SERCA activity in an amount sufficient to reduce or prevent restenosis in the subject. In a preferred embodiment, SERCA is SERCA1, e.g., SERCA1a or SERCA1b; SERCA2, e.g., SERCA2a or SERCA2b; or SERCA3, but preferably SERCA2a. The agent may also be administered in an amount effective to prevent endothelial cell proliferation or neointima formation.

The agent can be, e.g., a SERCA polypeptide or a functional fragment, variant or analog thereof having a SERCA activity, e.g., ATPase activity; a peptide or protein agonist of SERCA that increases the activity, e.g., the ATPase activity of SERCA (e.g., by increasing or stabilizing binding of SERCA to a binding partner, e.g., phospholamban); a small molecule that increases expression of SERCA, e.g., by binding to the promoter region of the SERCA gene; an antibody, e.g., an antibody (e.g., an intrabody) that binds to and stabilizes or assists the binding of SERCA to a SERCA binding partner (e.g., a SERCA binding partner described herein); or a nucleotide sequence encoding a SERCA polypeptide or functional fragment or analog thereof. The nucleotide sequence can be a genomic sequence or a cDNA sequence. The nucleotide sequence can include: a SERCA coding region; a promoter sequence, e.g., a promoter sequence from a SERCA gene or from another gene; an enhancer sequence; untranslated regulatory sequences, e.g., a 5' untranslated region (UTR), e.g., a 5'UTR from a SERCA gene or from another gene, a 3' UTR, e.g., a 3'UTR from a SERCA gene or from another gene; a polyadenylation site; an insulator sequence. In another embodiment, the level of SERCA protein is increased by increasing the level of expression of an endogenous SERCA gene, e.g., by increasing transcription of the SERCA gene or increasing SERCA mRNA stability. In a preferred embodiment, transcription of the SERCA gene is increased by: altering the regulatory sequence of the endogenous SERCA gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the SERCA gene to be transcribed more efficiently.

In a preferred embodiment, the agent is a vector that includes a nucleic acid encoding SERCA, e.g., SERCA1, e.g., SERCA1a or SERCA1b; SERCA2, e.g., SERCA2a or SERCA2b; or SERCA3, preferably a human SERCA. The vector can be any vector suitable for gene transfer. For example, the vector can be an adenoviral vector, e.g., recombinant type 2 or type 5 adenoviral vector; an adeno-associated virus, e.g., adeno-associated virus type 1, 2, 3, 4, 5 or 6, a lentiviral vector, or plasmid-based vector. The vector is preferably an adeno-associated virus-based vector or a lentivirus. Other vectors suitable for gene transfer, e.g., to cardiovascular tissue, are known in the art.

In a preferred embodiment, the SERCA encoding nucleic acid is under the control of a heterologous regulatory region, e.g., a heterologous promoter. The promoter can be, e.g., a smooth muscle specific promoter, such as a smooth muscle alpha actin promoter, SM22a promoter; cardiac specific promoter, such as a cardiac myosin promoter (e.g., a cardiac myosin light chain 2v promoter), troponin T promoter, or BNP promoter. The promoter can also be, e.g., a viral promoter, such as CMV promoter. The promoter can be an inducible promoter, e.g., one regulatable by an exogenous agent, e.g., FK506, FK1012, a steroid, or tetracycline.

The agent can be delivered by direct administration, e.g., injection (e.g., intra arterial, iv or im). In one embodiment, the agent is delivered directly to an affected vessel, e.g., artery. The agent can be coupled to a second agent, e.g., a delivery agent (e.g., an agent that protects the agent from degradation) or a targeting agent (e.g., for targeting to the vessel or targeting to the inside of a cell such as a smooth muscle cell, e.g., a liposome).

In a preferred embodiment, the subject is a human, e.g., a male or female human. For example, the human can be between 20-40 years of age, 40-60 years of age, or 60-70 years of age, or greater than 70 years of age. In some embodiments, the subject is identified by evaluation of the subject's health history, conducting a physical examination, or by performing clinical testing. A preferred subject is one who has undergone or will undergo (e.g., within 1, 2, 3, 5, 10, 15, 30, or more, days) angioplasty, balloon angioplasty, insertion of a prosthesis, insertion of a graft, insertion of a stent, catheterization, or arterial blockage evaluation. In one embodiment, the restenosis occurs after angioplasty. In another embodiment, the restenosis occurs after vascular stent placement. The blood vessel is preferably a coronary artery, and can also be, for example, a peripheral artery or a cerebral artery.

In a preferred embodiment, the method includes implanting a stent in an afflicted blood vessel of the subject, wherein the stent is coated with, or contains, the agent that increases SERCA activity, e.g., an agent described herein. In a preferred embodiment, the method includes implanting in a blood vessel of the subject a stent coated with, or containing, SERCA2a or an expression vector that includes a SERCA2a encoding nucleic acid.

In another embodiment, the agent is an agent that decreases phospholamban activity. An agent that inhibits phospholamban levels and/or activity can be one or more of: a phospholamban binding protein, e.g., a soluble phospholamban binding protein that binds and inhibits a phospholamban activity, e.g., SERCA2 binding activity; an antibody that specifically binds to the phospholamban protein, e.g., an antibody that disrupts phospholamban's ability to bind SERCA; a mutated inactive phospholamban or fragment thereof which, e.g., binds to a phospholamban binding partner (e.g., SERCA) but disrupts a phospholamban activity; a phospholamban nucleic acid molecule that can bind to a cellular phospholamban nucleic acid sequence, e.g., mRNA, and inhibit expression of the protein, e.g., an antisense molecule, phospholamban ribozyme or iRNA agent; an agent which decreases phospholamban gene expression, e.g., a small molecule which binds the promoter of phospholamban and decreases phospholamban gene expression. In another preferred embodiment, phospholamban is inhibited by decreasing the level of expression of an endogenous phospholamban gene, e.g., by decreasing transcription of the phospholamban gene. In a preferred embodiment, transcription of the phospholamban gene can be decreased by: altering the regulatory sequences of the endogenous phospholamban gene, e.g., by the addition of a negative regulatory sequence (such as a DNA-biding site for a transcriptional repressor), or by the removal of a positive regulatory sequence (such as an enhancer or a DNA-binding site for a transcriptional activator), activity, e.g., antisense nucleic acid at least partially complementary to a phospholamban DNA sequence, preferably a human phospholamban DNA sequence.

In one embodiment, the method includes preconditioning the heart of the subject; and delivering the agent into a cardiovascular cell of the preconditioned heart, wherein the flow of blood through the heart is reduced during the delivery of the agent. In a preferred embodiment, the agent is a nucleic acid (e.g., a SERCA2a encoding nucleic acid) administered into a vessel of the preconditioned heart, wherein the flow of blood through the heart is reduced during the delivery of the agent. In a preferred embodiment, preconditioning is accomplished using a catheter, e.g., a balloon catheter. "Preconditioning" refers to a naturally occurring protective mechanism by which a brief period of ischemia protects a tissue against adverse effects of a subsequent, prolonged period of ischemia. In the context of this method, "preconditioning" means inducing a state in which the heart is more resistant to damage from a second stoppage of flow. Preconditioning the heart muscle can be accomplished by a brief occlusion of a cardiac vessel (e.g., the left anterior descending artery) resulting in substantially increased expression of a gene subsequently transduced into the heart muscle. Preconditioning in the present method can be induced with a pharmacological agent, a mechanical manipulation, e.g., a catheter (e.g., a balloon catheter), or other surgical method.

In a preferred embodiment, the method includes evaluating the subject for a cardiovascular parameter, e.g., lumen loss, heart rate, heart contractility, ventricular function, e.g., left ventricular end-diastolic pressure (LVEDP), left ventricular systolic pressure (LVSP), $Ca^{2+}$ metabolism, e.g., intracellular $Ca^{2+}$ concentration or peak or resting $Ca^{2+}$, force generation, relaxation and pressure of the heart, a force frequency relationship, cardiocyte survival or apoptosis or ion channel activity, e.g., sodium calcium exchange, sodium channel activity, calcium channel activity, sodium potassium ATPase pump activity, activity of myosin heavy chain, troponin I, troponin C, troponin T, tropomyosin, actin, myosin light chain kinase, myosin light chain 1, myosin light chain 2 or myosin light chain 3, IGF-1 receptor, PI3 kinase, AKT kinase, sodium-calcium exchanger, calcium channel (L and T), calsequestrin or calreticulin. The evaluation can include performing angiography (e.g., quantitative angiography) and/or intravascular ultrasound (IVUS), e.g., before, after, or during the treatment.

In a preferred embodiment, a pharmaceutical composition including one or more of the agents described herein is administered in a pharmaceutically effective dose.

In a preferred embodiment, the administration of an agent which increases SERCA expression, levels or activity can be initiated: when the subject begins to show signs of restenosis, e.g., as evidenced by an decrease of more than 5, 10, 20, or 30% in lumen; when a coronary vascular condition is diagnosed; at the time a treatment for a coronary vascular condition is begun or begins to exert its effects (e.g., during surgery to implant a stent); or generally, as is needed to maintain heart function.

The period over which the agent is administered (or the period over which clinically effective levels are maintained in the subject) can be long term, e.g., for six months or more or a year or more, or short term, e.g., for less than a year, six months, one month, two weeks or less. Although an agent can be administered in a short term, or once, expression of a nucleic acid in the agent can be sustained, e.g., for at least one, two, three, four, or six months. Promoters can be selected that are inducible, e.g., to limit or prolong the period of expression.

In another aspect, the disclosure features a stent coated with, or containing an agent that can increase SERCA expression, e.g., an agent described herein. For example, the agent is a nucleic acid. The nucleic acid can be packaged in a viral or non-=viral particle. The stent can include, e.g., at least $1\times10^9$, $1\times10^{10}$, $1\times10^{11}$, $1\times10^{12}$, $1\times10^{13}$, $1\times10^{14}$, $1\times10^{15}$, or $1\times10^{16}$ units (e.g., particles), or, for example, between $1\times10^9$ to $1\times10^{18}$ or $1\times10^{11}$ to $1\times10^{16}$.

In a preferred embodiment, the agent is a nucleic acid encoding SERCA, e.g., SERCA1, e.g., SERCA1a or SERCA1b; SERCA2, e.g., SERCA2a or SERCA2b; or SERCA3. In a preferred embodiment, the SERCA encoding nucleic acid is under the control of a heterologous regulatory region, e.g., a heterologous promoter. The promoter can be, e.g., a smooth muscle specific promoter, such as a smooth muscle alpha actin promoter, SM22a promoter; cardiac specific promoter, such as a cardiac myosin promoter (e.g., a cardiac myosin light chain 2v promoter), troponin T promoter, or BNP promoter. The promoter can also be, e.g., a viral promoter, such as CMV promoter.

In another embodiment, the agent is an antisense nucleic acid at least partially complementary to a phospholamban DNA sequence, preferably a human phospholamban DNA sequence.

Although a stent described herein is preferably for use in a blood vessel, it can also be used in other tissues such as those forming a cavity, orifice or duct, in which restenosis can occur. Causes of such restenosis include, for example, organ transplantation.

In some embodiments, a stent described herein, in addition to being coated with, or containing, an agent that increases SERCA expression, can also be coated with a second therapeutic agent. For example, the stent can also contain one or more of: rapamycin, taxol and actinomycin-D.

In another aspect, the disclosure features a kit. The kit includes: (a) an agent that increases SERCA, e.g., SERCA2a, activity (e.g., SERCA, a nucleic acid encoding SERCA, or an antisense nucleic acid at least partially complementary to a phospholamban nucleic acid), and (b) informational material relating to restenosis. Optionally, the kit includes a stent containing, or coated with, the agent. The informational material can include instructions for using the kit to prevent or treat restenosis.

In another aspect, the disclosure features a stent that includes an antibody (e.g., a full length antibody or an antibody fragment, e.g., a Fab, Fc, scFv, etc). The antibody binds to a coat protein of a viral particle, e.g. a viral particle described herein. The stent can be used to deliver viral particles that contain any nucleic acid of interest, e.g., a therapeutic nucleic acid, e.g., a nucleic acid described herein. For example, the antibody can have an antigen binding site that interacts with a coat protein of an adenovirus, or an adeno-associated virus, or a lentivirus, e.g., a retrovirus.

As used herein, a "stent" is a medical device configured for implantation in a body lumen to prevent or inhibit the closing of the lumen. A stent can be configured to be implanted in, e.g., a blood vessel such as an artery, or other body cavity, orifice or duct, such as a ureter. A stent is typically made of biocompatible metal or plastic.

As used herein, a stent "coated with or containing" an agent means a stent having the agent either affixed to its surface or contained within it, so as to permit release of the agent from the stent and, hence, delivery of the agent to tissue in proximity with the stent. A stent can also include a slow-release formulation of the agent, e.g., to release the agent over time. An agent can be affixed by non-covalent interactions or by covalent interactions, e.g., covalent interactions that are disrupted overtime.

Ability of an agent to function to a required degree can be to an extent detectable as significant by one skilled in the art or to a statistically significant degree.

DETAILED DESCRIPTION

Figure 1:
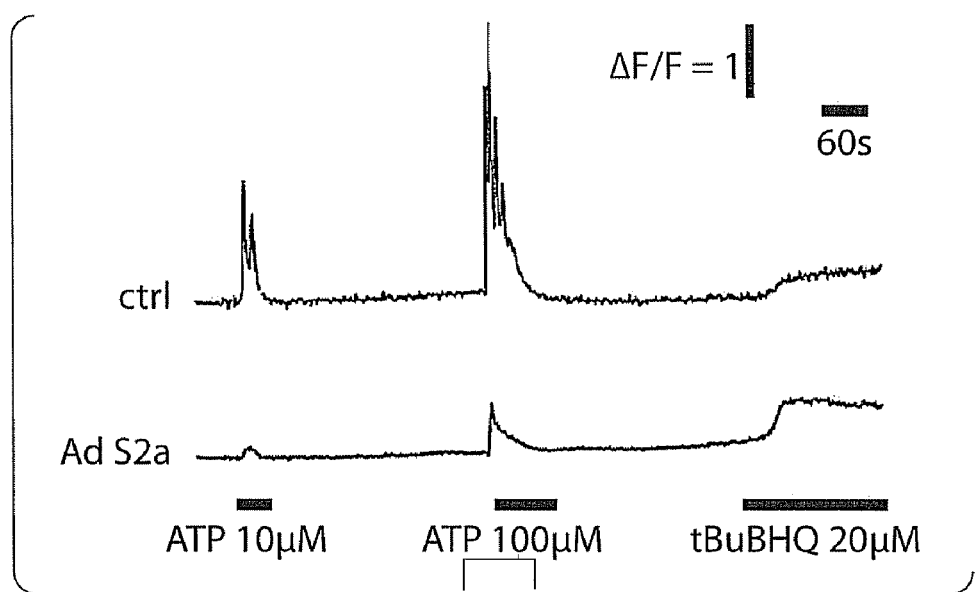
FIG. 1 is a set of traces showing the ATP- and tBuBHQ-induced increase in cytosolic [Ca2+] in control conditions (top) or in cells infected with adenovirus SERCA2a vector (Ad S2a) (bottom).

The restenosis rates for the most common treatments for coronary vascular conditions are shown in Table 1.

TABLE 1

| | RESTENOSIS RATE | | |
|---|---|---|---|
| Condition | Angioplasty | Stent | Rapamycin Coated Stents |
| Myocardial Infarction | 30% | 20% | <10% |
| Vein Graft Occlusion | 50-60% | 30% | — |
| Chronic Coronary Artery Disease | 40% | 20% | <10% |

Proliferation of vascular smooth muscle cells (VSMC) is thought to be a key factor in the development of atherosclerosis and restenosis after balloon injury and is associated with dedifferentiation of the VSMC. Alterations in expression of proteins involved in calcium homeostasis have been reported. Differentiated smooth muscle cell exhibits different Ca2+ signals including localized transient release through the ryanodine receptors in the form of Ca2+ sparks and Ca2+ waves of different amplitude and frequency. Proliferation of VSMC is accompanied by replacement of the L-type Ca2+ channels by the T-type, loss of ryanodine receptors and of SERCA2a, and enhanced capacitative Ca2+ entry.

The inventors have found that increasing SERCA (e.g., SERCA2a) activity in a subject can prevent or reduce restenosis. The methods described herein, e.g., methods of preventing or reducing restenosis by increasing SERCA activity, e.g., by gene transfer of SERCA, can improve calcium handling without causing apoptosis. Other advantages of the methods and compositions described herein include: decreased proliferation of smooth muscle cells without causing apoptosis and cell death; lack of toxicity in other tissues; beneficial effects within the myocardium; prevention of smooth muscle death and maintenance of the integrity of the wall.

Sarcoplamic Reticulum (SR) $Ca^{2+}$ ATPase (SERCA)

The sarcoplasmic reticulum (SR) is an internal membrane system, which plays a critical role in the regulation of cytosolic $Ca^{2+}$ concentrations and thus, excitation-contraction coupling in muscle. In cardiac cells release of $Ca^{2+}$ from the SR leads to contraction whereas in smooth muscle cells it induces vasorelaxation through activation of $Ca^{2+}$ activated potassium channels and hyperpolarisation of the cell. Control of the cytosolic $Ca^{2+}$ concentration involves the active re-uptake of $Ca^{2+}$ into the SR lumen by a $Ca^{2+}$-ATPase. In cardiac and smooth muscles, the SR $Ca^{2+}$-ATPase activity (SERCA2a) is under reversible regulation by phospholamban.

Defects in SR $Ca^{2+}$ cycling have a crucial role in progression of cardiac hypertrophy and failure. Cardiac hypertrophy as well as its deleterious effects on contractile function can be prevented by activating SR $Ca^{2+}$ uptake either by SERCA2a gene transfer or by decreasing the inhibitory effect of phospholamban on SERCA 2a (reviewed in Kaprielian et al., 2002, Basic Res Cardiol. 97 Suppl 1:I136-45).

The sequence of human SERCA proteins are known in the art (see, e.g., Lytton and MacLennan, 1988, J. Biol. Chem. 263(29), 15024-15031; Genbank Accession Nos. NP_001672; P16615; NP_733765).

Exemplary Gene Transfer

The nucleic acids described herein, e.g., a SERCA encoding nucleic acid, can be incorporated into a gene construct to be used as a part of a gene therapy protocol. Methods for gene transfer in vivo are known in the art. Approaches include insertion of the subject gene in viral vectors including recombinant retroviruses, adenovirus (e.g., replication deficient, first generation, or gutted, second generation, adenovirus), adeno-associated virus (e.g., any of types 1-6), lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

Gene transfer into cardiovascular tissue, for example, has been successful using adenovirus (Ad) vectors with strong, non-tissue specific gene expression cassettes driven by cytomegalovirus (CMV) or Rous sarcoma virus (RSV) promoters. Clinical trials involving transduction of cardiac cells with viral vectors to deliver angiogenic factors such as vascular endothelial cell growth factor (VEGF), fibroblast growth factor (FGF) and hepatocyte growth factor (HGF) have been ongoing. Intra-aorta or intracoronary injection of virus has been used in vivo in animal models. In one study, intracardiac injection of an Ad-SERCA2a viral vector in rats was sufficient to induce physiological improvement in calcium handling. See Miyamoto et al., 2000, Proc. Natl. Acad. Sci. USA 97:793-98. Adenoviral vectors have also been used in vivo to express β2 adrenergic receptor (β-AR) (see Maurice et al. 1999, J. Clin. Invest. 104:21-9 and Shah et al., 2001, Circulation 103:1311). As is known from studies on cystic fibrosis, transduction of all cells in a tissue is not required for improved function. For example, expression of the wild type sodium channel in as few as 6-10% of cells within an epithelial sheet lacking a functional sodium channel is sufficient for normal sodium ion transport (Johnson et al, 1992, Nat. Genet 2:21-5). This is known as the bystander effect.

Tissue specific promoters have been used to increase specificity of myocardial gene expression (Rothmann et al., 1996, Gene Ther. 3:919-26). Another strategy to restrict expression of transferred genes to the heart has involved direct injection of a viral vector into the myocardium (Gutzman et al, 1993, Cric. Res. 73: 1202-7; French et al., 1994, Circulation. 90:2414-24). Another attempt involved intrapericardial virus vector injection combined with proteinase treatment (Fromes et al., 1999, Gene Ther. 6:683-8). These manipulations achieved local gene delivery, although with some drawbacks, due to a lack of intense viral vector diffusion.

The efficiency of cardiomyocyte gene delivery by an adeno-associated virus (AAV) vector was documented in vitro using cultured rat neonatal cells, as well as in an ex vivo system using rat papillary muscle immersion (Maeda et al., 1998, J. Mol. Cell. Cardiol. 30:1341-8). Ex vivo AAV vector transfer followed by syngeneic heart transplantation was reported to achieve high efficiency marker gene expression (Svensson et al., 1999, Circulation. 99:201-5).

Methods of achieving a high level of in vivo cardiotopic gene transfer with high consistency (average 60-70% of cardiac myocytes) are described, e.g., in US Published Application 20020032167. Other methods for the preparation and use of viral vectors are described in WO 96/13597, WO 96/33281, WO 97/15679, and Trapnell et al., 1994, Curr. Opin. Biotechnol. 5(6):617-625; Ardehali et al., 1995, J. Thorac. Cardiovasc. Surg. 109:716-720; Dalesandro et al., 1996, J. Thorac. Cardiovasc. Surg. 111:416-422; Sawa et al., 1995, Circ 92, II479-11482; Lee et al., 1996, J. Thorac. Cardiovasc. Surg. 111, 246-252; Yap et al., 19996, Circ. 94, I-53; and Pellegrini et al., 1998, Transpl. Int. 11, 373-377.

A subject polynucleotide can also be administered using a non-viral delivery vehicle. "Non-viral delivery vehicle" (also referred to herein as "non-viral vector") as used herein is meant to include chemical formulations containing naked or condensed polynucleotides (e.g., a formulation of polynucleotides and cationic compounds (e.g., dextran sulfate)), and naked or condensed polynucleotides mixed with an adjuvant such as a viral particle (i.e., the polynucleotide of interest is not contained within the viral particle, but the transforming formulation is composed of both naked polynucleotides and viral particles (e.g., adenovirus particles) (see, e.g., Curiel et al. 1992 Am. J. Respir. Cell Mol. Biol. 6:247-52)). Thus "non-viral delivery vehicle" can include vectors composed of polynucleotides plus viral particles where the viral particles do not contain the polynucleotide of interest. "Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed by Felgner et al (U.S. Pat. Nos. 5,264,618 and 5,459,127; PNAS 84:7413-7417, 1987; Annals N.Y. Acad. Sci. 772:126-139, 1995); they may also consist of neutral or negatively charged phospholipids or mixtures thereof including artificial viral envelopes as disclosed by Schreier et al. (U.S. Pat. Nos. 5,252,348 and 5,766,625).

Non-viral delivery vehicles include polymer-based carriers. Polymer-based carriers may include natural and synthetic polymers and co-polymers. Preferably, the polymers are biodegradable, or can be readily eliminated from the subject. Naturally occurring polymers include polypeptides and polysaccharides. Synthetic polymers include, but are not limited to, polylysines, and polyethyleneimines (PEI; Boussif et al., PNAS 92:7297-7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

In clinical settings, the gene delivery systems for the therapeutic gene can be introduced into a patient by any of a number of methods, each of which is familiar in the art. For instance, a pharmaceutical preparation of the gene delivery system can be introduced systemically, e.g, by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

The polynucleotide to be delivered can also be formulated as a DNA- or RNA-liposome complex formulation. Such complexes comprise a mixture of lipids which bind to genetic material (DNA or RNA) by means of cationic charge (electrostatic interaction). Cationic liposomes which may be used in the present invention include 3β-[N—(N',N'-dimethylaminoethane)-carbamoyl]-cholesterol (DC-Chol), 1,2-bis (oleoyloxy-3-trimethylammonio-propane (DOTAP) (see, for example, WO 98/07408), lysinylphosphatidylethanola-mine (L-PE), lipopolyamines such as lipospermine, N-(2-hydroxyethyl)-N,N-dimethyl-2,3-bis(dodecyloxy)-1-propan-aminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy)propyl-N,N,N-triethylammonium (DOTMA), DOSPA, DMRIE, GL-67, GL-89, Lipofectin, and Lipofectamine (Thiery et al. (1997) Gene Ther. 4:226-237; Felgner et al., Annals N.Y. Acad. Sci. 772:126-139, 1995; Eastman et al., Hum. Gene Ther. 8:765-7.73, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also encompassed are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

Exemplary Methods of Treatment

The present invention includes within its scope the use of a composition for treating restenosis, comprising an agent that increases SERCA, e.g., SERCA2a, activity. The agent can be, e.g., a nucleic acid encoding SERCA in the form of expression vector containing a DNA encoding SERCA2, preferably SERCA2a, in association with a pharmaceutically acceptable carrier, excipient or other additive, if necessary. In another embodiment, the agent is an antisense nucleic acid at least partially complementary to a phospholamban nucleic acid sequence in association with a pharmaceutically acceptable carrier, excipient or other additive, if necessary. Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The compositions may additionally include lubricating agents, wetting agents, flavoring agents, emulsifiers, preservatives and the like.

The compositions described herein can be formulated so as to provide quick, sustained or delayed release of the active ingredient after administration to a patient by employing any of the procedures well known in the art.

In a preferred embodiment, the agent is formulated for intracardiac or intra vessel administration. Such direct administration can be accomplished thorough, e.g., coating the agent on a stent to be implanted into a vessel of the subject. The effective amount of a nucleic DNA encoding SERCA2a as an active ingredient may range from about 0.05 to 500 mg/kg, preferably 0.5 to 50 mg/kg body weight, and can be administered in a single dose or in divided doses. However, it should be understood that the amount of the active ingredient actually administered ought to be determined in light of various relevant factors including the condition to be treated, the age and weight of the individual patient, and the severity of the patient's symptom; and, therefore, the above dose should not be intended to limit the scope of the invention in any way.

Exemplary Stents

The invention also includes a stent coated with, or containing, an agent that increase SERCA, preferably SERCA2a, activity, e.g., an agent described herein. Methods for preparing stents (both biodegradable and non-biodegradable) for delivering a therapeutic agent are well known (see, e.g., U.S. Pat. Nos. 5,163,952, 5,304,121, 6,391,052, 6,387,124, 6,379, 382, and 6,358,556, 6,605,110, 6,605,114, 6,572,645, 6,569, 194, 6,545,748, 6,541,116, 6,527,801, 6,506,437). In one embodiment, a stent described herein is coated with a therapeutic agent, e.g., an agent described herein, such as a SERCA nucleic acid described herein, using techniques known in the art.

In one embodiment, the stent is a stainless steel stent or nytinol mesh like devices. For example, a stent can be delivered into the coronary artery on a catheter during a PCI procedure (percutaneous coronary intervention). A stent can be deployed in the artery by either expansion by a balloon or by a self expanding delivery design. Exemplary commercially available stents include Gianturco-Roubin Stents (e.g., from Cook Cardiology), Multilink, Duet, Tetra, Penta, Zeta Stents (e.g., from Guidant); Nir, Wall Stents, Taxus (e.g., from SCIMED/Boston Scientific), GFX/S series Stents (e.g., from Medtronic/AVE), velocity and Cypher stents (e.g., from Johnson & Johnson/Cordis)

For example, a stent can be coated with a polymeric cation that can mediate nucleic acid condensation or compaction, e.g., as described in U.S. Pat. No. 6,596,699. Linear polycations such as poly-L-lysine, polyornithine, polyarginine and the like can be used. The polymers may be homopolymers, such as polylysine, polyornithine, or polyarginine, or may be heteropolymers, including random polymers formed of lysine, ornithine, arginine and the like. More complex molecules may also be employed as polycations, such as branched or linear polyethylenimine and the like. Any of a variety of naturally occurring nucleic acid binding agents may be employed, such as spermine or spermidine, and are including within the definition of polycation. Protamine can similarly be employed, as can any of a variety of histones. Polyamidoamine dendrimers may similarly be employed, wherein terminal amino groups bind the nucleic acid by electrostatic means, resulting in positively charged condensates. The polycation may be specifically modified to provide optimal characteristics to form the desired condensate. For example, a repeating lysine chain of 18 residues followed by a tryptophan and an alkylated cysteine residue has been reported to form condensates with properties at least equal to polylysine. McKenzie et al., J. Peptide Res. 54:311-318 (1999). In general, the polycation is positively charged, and has a net positive charge at about pH 6 to about 8 or has more than about five positively charged residues. The polycation has a higher number of positive charges compared to the number of negative charges. A polycation includes natural nucleic acid-binding proteins and recombinant nucleic acid-binding protein, such as homo- or hetero-polymers of amino acids or synthetic compounds that bind to one or more nucleic acid sequences found within natural or recombinant nucleic acid molecules and results in nucleic acid condensation.

An additional method of coating a therapeutic nucleic acid onto a medical device such as a stent involves coating the medical device with a swellable hydrogel polymer as described, e.g., in U.S. Pat. No. 5,674,192 or 6,409,716. The hydrogel coating is characterized by the ability to incorporate a substantial amount of the nucleic acid, typically in aqueous solution form, and is swellable such that the aqueous solution can be effectively squeezed out of the coating when pressure is applied, e.g., by inflation or expansion of the stent. Administration of the drug in this way enables the drug to be site-specific, such that release of high concentrations can be limited to direct application to the affected tissue.

Other methods of coupling a therapeutic agent, such nucleic acid, to a stent or other medical device are known in the art, see for example, U.S. Pat. No. 6,024,918, U.S. Pat. No. 6,506,408; U.S. Pat. No. 5,932,299.

In some embodiments, a stent described herein, in addition to being coated with, or containing, an agent that increases SERCA expression, can also be coated with a second therapeutic agent. For example, the stent can also contain one or more of rapamycin, taxol and actinomycin-D, a thrombin inhibitor, an antithrombogenic agent, a thrombolytic agent, a fibrinolytic agent, a vasospasm inhibitor, a calcium channel blocker, a vasodilator, an antihypertensive agent, an antimicrobial agent, an antibiotic, an inhibitor of surface glycoprotein receptors, an antiplatelet agent, an antimitotic, a microtubule inhibitor, an antisecretory agent, an actin inhibitor, a remodeling inhibitor, an antisense nucleotide, an antimetabolite, an antiproliferative, an anticancer chemotherapeutic agent, an anti-inflammatory steroid or non-steroidal antiinflammatory agent, an immunosuppressive agent, a growth hormone antagonist, a growth factor, a dopamine agonist, a radiotherapeutic agent, a peptide, a protein, an enzyme, an extracellular matrix component, a free radical scavenger, a chelator, an antioxidant, an antipolymerase, an antiviral agent, a photodynamic therapy agent, and a gene therapy agent, e.g., a second gene therapy agent. In one embodiment, the subject is also administered a second agent, e.g., separately from the agent that increases SERCA activity. For example, the subject can be orally administered aspirin or an oral anti-platelet drug (e.g., PLAVIX® or TICLID®).

Exemplary Kits

The agent described herein (e.g., SERCA nucleic acid or polypeptide) can be provided in a kit. The kit includes (a) the agent, e.g., a composition that includes the agent, (b) informational material, and optionally (c) a stent. The informational material can be descriptive, instructional, marketing or other material that relates to the methods described herein and/or the use of the agent for the methods described herein. For example, the informational material relates to restenosis.

In one embodiment, the informational material can include instructions to administer the agent in a suitable manner to perform the methods described herein, e.g., in a suitable dose, dosage form, or mode of administration (e.g., a dose, dosage form, or mode of administration described herein). In another embodiment, the informational material can include instructions to administer the agent to a suitable subject, e.g., a human, e.g., a human having, or at risk for, restenosis. For example, the material can include instructions to administer the agent to a subject who has had, is having or will have angioplasty.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the agent and/or its use in the methods described herein. Of course, the informational material can also be provided in any combination of formats.

In addition to the agent, the composition of the kit can include other ingredients, such as a solvent or buffer, a stabilizer, a preservative, and/or a second agent for treating a condition or disorder described herein. Alternatively, the other ingredients can be included in the kit; but in different compositions or containers than the agent. In such embodiments, the kit can include instructions for admixing the agent and the other ingredients, or for using the agent together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent. For example, the kit includes a plurality of syringes, ampules, foil packets, or blister packs, each containing a single unit dose of the agent. The containers of the kits can be air tight and/or waterproof.

The kit optionally includes a device suitable for administration of the composition, e.g., a stent, syringe, or any useful delivery device. In a preferred embodiment, the device is a stent.

Generation of Variants: Production of Altered DNA and Peptide Sequences by Random Methods Amino acid sequence variants of SERCA or fragments thereof can be prepared by a number of techniques, such as random mutagenesis of DNA which encodes a SERCA or a region thereof. Useful methods also include PCR mutagenesis and saturation mutagenesis. A library of random amino acid sequence variants can also be generated by the synthesis of a set of degenerate oligonucleotide sequences.

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

Generation of Variants: Production of Altered DNA and Peptide Sequences by Directed Mutagenesis Non-random or directed mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* (1978) USA, 75: 5765).

Cassette Mutagenesis

Another method for preparing variants, cassette mutagenesis, is based on the technique described by Wells et al. (*Gene,* 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate variants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening peptides, e.g., synthetic peptides, e.g., small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with SERCA. These may include, e.g., agonists, superagonists, and antagonists of SERCA. (The subject protein and a protein it interacts with are used as the bait protein and fish proteins). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., SERCA or active fragments thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370-1371; and Goward et al. (1992) *TIBS* 18:136-140). This technique was used in Sahu et al. (1996) J. Immunology 157:884-891, to isolate a complement inhibitor. In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007-16010; Griffiths et al. (1993) *EMBO J* 12:725-734; Clackson et al. (1991) *Nature* 352:624-628; and Barbas et al. (1992) *PNAS* 89:4457-4461).

A common approach uses the maltose receptor of *E. coli* (the outer membrane protein, LamB) as a peptide fusion partner (Charbit et al. (1986) *EMBO* 5, 3029-3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387-392), PhoE (Agterberg, et al. (1990) *Gene* 88, 37-45), and PAL (Fuchs et al. (1991) *Bio/Tech* 9, 1369-1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984-993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080-1083). Surface proteins of other bacterial species have also served as peptide fusion partners. Examples include the *Staphylococcus* protein A and the outer membrane protease IgA of *Neisseria* (Hansson et al. (1992) *J. Bacteriol.* 174, 4239-4245 and Klauser et al. (1990) *EMBO J.* 9, 1991-1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865-1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378-6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233-1251). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233-1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204, 357-364). To identify the sequences of the active peptides one sequences the DNA produced by the phagemid host.

For example, one or more residues (e.g., between one and six residues or one and three residues) in a SERCA protein can differ from wild-type or can be deleted. For example, the N-terminal first and/or second residue (e.g., after removal of a signal sequence) can be deleted, and the C-terminal-most first and/or second residue can be deleted. Selected transmembrane residues can be altered, e.g., with similar hydrophobic residues. The protein may include other substitutions, e.g., conservative substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Secondary Screens for Inhibitors of the Alternative Pathway

The high through-put assays described above can be followed (or substituted) by secondary screens, e.g., the following screens, in order to identify biological activities which will, e.g., allow one skilled in the art to differentiate agonists from antagonists. The type of a secondary screen used will depend on the desired activity that needs to be tested. Several such assays are described below. For example, an assay can be developed in which the ability to increase or mimic SERCA activity can be used to identify SERCA agonists from a group of peptide fragments isolated though one of the primary screens described above.

Binding Assays

SERCA can bind to a SERCA binding partner, e.g., phospholamban or sarcolipin. The ability of a SERCA variant to bind a binding partner, e.g., phospholamban or sarcolipin, is an assayable activity of SERCA function. In addition, a binding assay, e.g., a binding assay described herein, can be used to evaluate: (a) the ability of a test agent to bind SERCA; (b) the ability of a test agent to inhibit binding of SERCA to a binding partner, e.g., the ability of a test agent to inhibit or disrupt SERCA binding to phospholamban or sarcolipin; the ability of a test agent to stabilize or increase binding of a complement component to a binding partner, e.g., the ability of a test agent to stabilize or increase SERCA binding to phospholamban or sarcolipin.

As SERCA, e.g., human SERCA, has been cloned and produced recombinantly, it is readily available as a reagent to be used in standard binding assays known in the art, which include, but are not limited to: affinity chromatography, size exclusion chromatography, gel filtration, fluid phase binding assay; ELISA (e.g., competition ELISA), immunoprecipitation.

Peptide Mimetics

The invention also provides for production of domains of SERCA, to generate mimetics, e.g. peptide or non-peptide agents, e.g., agonists.

Non-hydrolyzable peptide analogs of critical residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al.

(1986) J Chem Soc Perkin Trans 1:1231), and b-aminoalcohols (Gordon et al. (1985) Biochem Biophys Res Commun 126:419; and Dann et al. (1986) Biochem Biophys Res Commun 134:71).

Exemplary Modes of Administration

An agent that modulates SERCA signaling, e.g., an agent described herein, can be administered to a subject by standard methods. For example, the agent can be administered by any of a number of different routes including by introduction into a lumen of the circulatory system, e.g., the lumen of an artery, vein, or organ, e.g., the heart. In another embodiment, the agent is administered by injection, e.g., intra-arterially, intramuscularly, or intravenously. The agent can be packaged in a viral particle, and formulated with materials compatible with maintaining ability of the viral particle to introduce the nucleic acid into a cell, e.g., when the viral particle is introduced into a subject.

The agent, e.g., a SERCA nucleic acid molecule, polypeptide, fragments or analog, modulators (e.g., organic compounds and antibodies (also referred to herein as "active compounds") can be incorporated into pharmaceutical compositions suitable for administration to a subject, e.g., a human. Such compositions typically include the polypeptide, nucleic acid molecule, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

In a preferred embodiment, the pharmaceutical composition is injected into an affected vessel, e.g., an artery, e.g., a coronary artery. In another embodiment, the pharmaceutical composition is delivered in association with a medical device that is introduced into an affected vessel, e.g., a stent that is introduced into the affected vessel. Additional exemplary modes of administration are described, e.g., in U.S. Ser. No. 10/914,829.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, the drawings, and the claims.

EXAMPLES

Example 1

SERCA 2a Expression in Growing VSMC Inhibits Proliferation

Rat aortic SMC were isolated from the media of the thoracic aorta from male Wistar rats as and cultured in DMEM supplemented with 1% penicillin-streptomycin-amphotericin mixture (ICN) and 10% fetal calf serum (FCS). At confluence they were passaged using trypsin. Cells between passage 2 to 8 were used.

The rat VSMC were infected with adenovirus SERCA2a vector essentially as described in del Monte et al., 2001, *Circulation* 104:1424. Briefly, human SERCA2a cDNA was subcloned into the adenoviral shuttle vector (pAd.TRACK), which uses the cytomegalovirus (CMV) long terminal repeat as a promoter to make Ad-S2a vector. The shuttle vector used also has a concomitant green fluorescent protein (GFP) under the control of a separate CMV promoter. An adenovirus containing both β-galactosidase and GFP controlled by separate CMV promoters (Ad-βGal-GFP) was used as control. The adenoviruses were propagated in 293 cells. The recombinant adenoviruses were tested for the absence of wild-type virus by polymerase chain reaction of the early transcriptional unit E1.

Figure 2A:
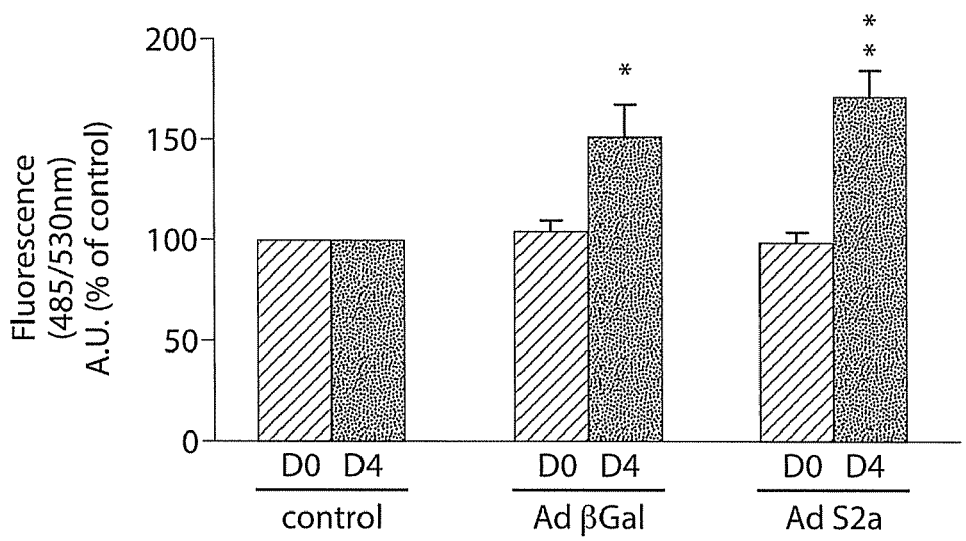
FIG. 2 is a set of graphs and micrographs showing the effects of SERCA2a on VSMC. SERCA 2a expression in growing VSMC blocked proliferation. (A) monitoring of adenoviral infection by GFP fluorescence (485/530 nm) in cultured VSMC (D0, day of infection; D4, day 4 after infection); (B) analysis of expression of SERCA2 by Western blot at D4 in Ad-infected and control VSMC; 40 μg of total protein extract were loaded on each line; and (C) effect of infection by Ad-βGal and Ad-S2a on proliferation of VSMC.
Figure 2B:
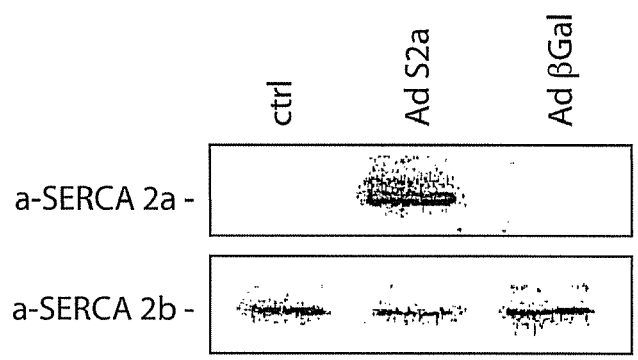

Adenoviral infection was followed by monitoring the fluorescence of GFP. Significant increase in fluorescence was observed 4 days after infection (FIG. 2A). Control cells as well as Ad-βGal-GFP infected cells did not express SERCA 2a. A high amount of SERCA 2a was present in Ad S2a-infected cells without much change in the level of SERCA 2b (FIG. 2B).

Figure 2C:
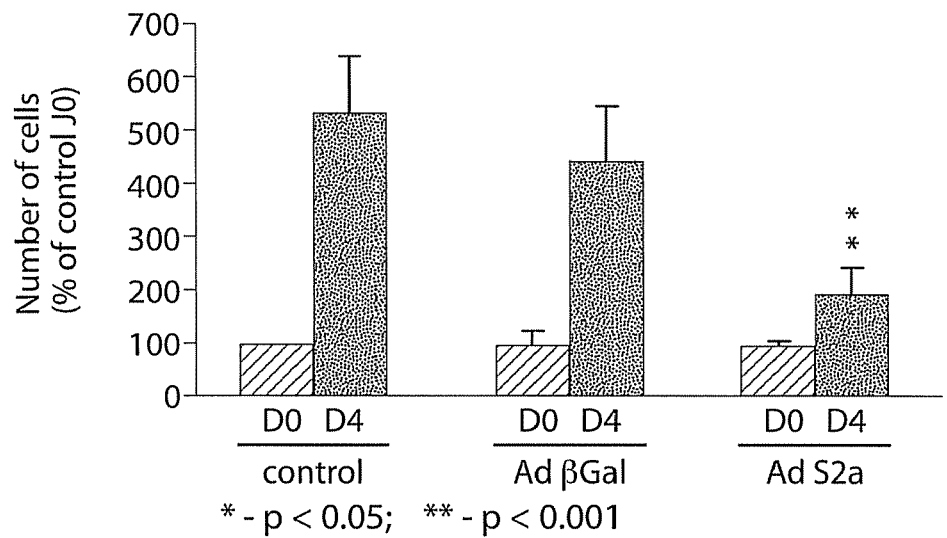

Proliferation of VSMC was measured by using the colorimetric-based CELLTITER96® Cell Proliferation Assay kit (Promega) according to manufacturer instructions. Between day 0 and day 4, the number of cells in control conditions and in cells infected with Ad βpal had increased 5 times whereas the number of Ad S2a-infected cells increased significantly less ($p<0.01$) (FIG. 2C), indicating that SERCA 2a prevents VSMC proliferation. This was also confirmed by immunolabelling with a-PCNA (FIG. 2D). Indeed, the cell labelled with a-SERCA 2a did not express PCNA, a marker of S phase, whereas PCNA was present in non-infected cells or in cells infected with Ad-βGal.

Accordingly, SERCA 2a prevents VSMC proliferation in vitro.

Example 2

SERCA 2a Expression Blocks the Cell Cycle at the G1 Phase and Prevents Entry in the S Phase The absence of PCNA in Ad-S2a-infected cells indicated that the cells did not enter the S phase.

VSMCs were harvested by trypsinization and stained with propidium iodide and the DNA content and cell cycle were determined. Fluorescence of the nuclei after labelling with propidium iodide was analysed using a flowcytometer. In the control situation and in Ad-βGal-GFP infected cells the percentage of S gated events was approximately 50% and 46% respectively, whereas it was only approximately 30% in Ad-S2a-infected cells. No cells were in the subG1, indicating the absence of apoptosis.

Example 3

SERCA 2a Expression Prevents NFAT Activation

Figure 3A:
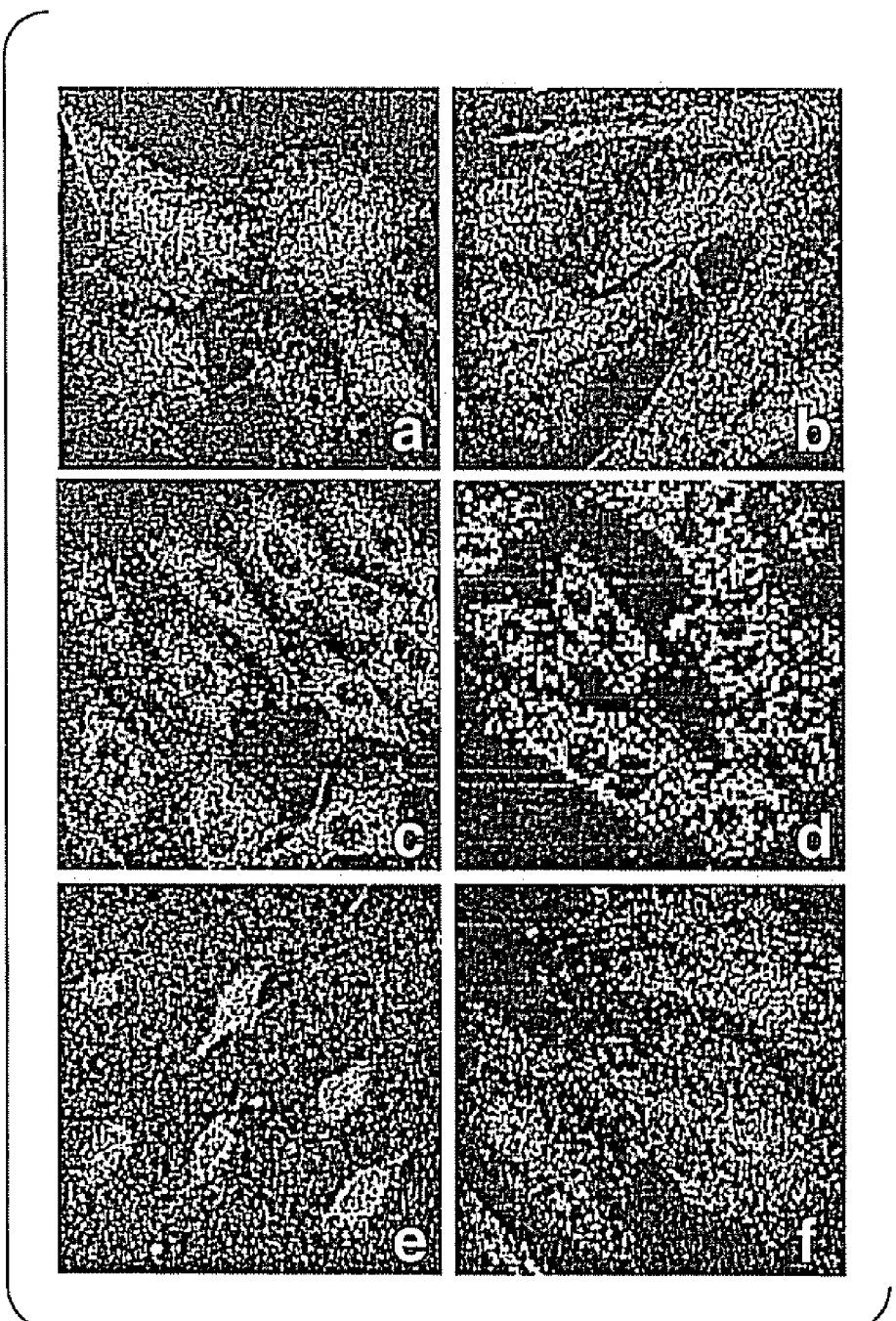
FIG. 3 illustrates the effect of SERCA2a expression on NFAT nuclear translocation in one implementation. (A) immunolabelling with a-NFAT: a—Ad bGal infected, b—control, c—Ad S2a infected, d—control+CsA (5 μM, 24 h), e—Ad S2a infected+Tg (1 μM, 1 h), f—control+Tg (1 μM, 1 h). (B) western blot analysis of cytosolic and nuclear extract prepared from control and Ad-infected SMC. Immunohybridisation with a-NFATc1. (C) analysis of NFAT-binding activities from control and Ad-infected SMC. EMSA experiments were performed with the P32-labelled NFAT probe.
Figure 3B:
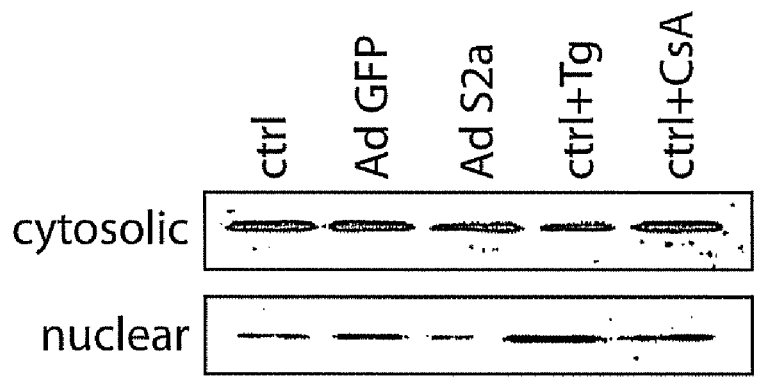
Figure 3C:
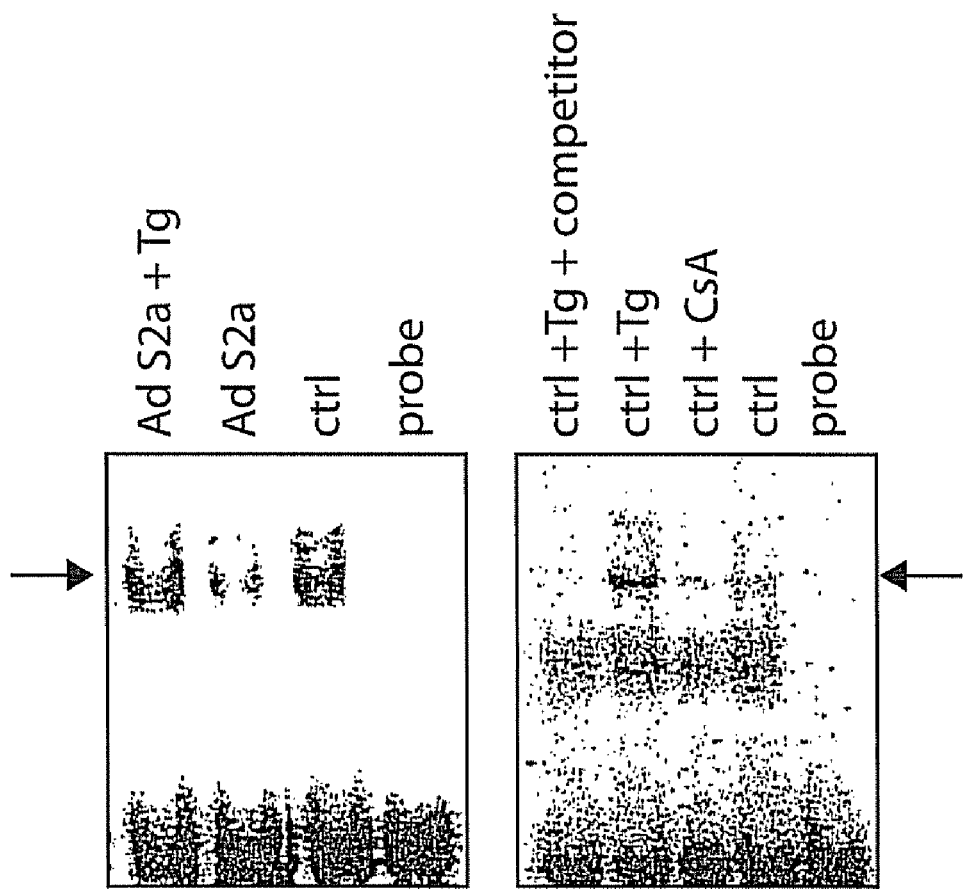

SERCA2a overexpression inhibits smooth muscle activation of NFAT and calcineurin, downstream markers of hypertrophy and proliferation (FIG. 3)

Example 4

Adenovirus-Mediated Expression of SERCA2a in Balloon-Injured Rat Carotid Arteries Decreases Restenosis Balloon injured rat carotid arteries were infected with $10^{10}$ pfu Ad-S2a (n=4) or Ad-βGal-GFP (control virus). Fourteen days after infection, quantitative morphometry was performed on 5-µm sections from the transduced segment by an investigator blinded to the experimental procedure.

At fourteen days after balloon injury and infection, the intima/media ratio was significantly lower in arteries infected with Ad-S2a (0.16±0.08) than in control infected arteries (0.73±0.12). $P<0.05$ for both.

Example 5

Other Methods

Western blot analysis and immunofluorescence: Total cell lysates were prepared according to standard protocol (Upstate biotechnology, Technical Support). Cytosolic and nuclear fractions were obtained by hypotonic lysis. The protein content was determined by using Bradford Protein Assay Reagent Kit (Bio-Rad). Lysates were matched for protein concentration, resolved by SDS-PAGE and transferred to Hybond-C (Amersham). The primary antibody was a-NFATc1 from Santa Cruz Biotechnology, Inc (K-18). Proteins were visualized using a goat anti-rabbit secondary antibody conjugated to horseradish peroxidase and enhanced chemiluminescence's detection system (ECL+, Amersham).

Immunofluorescence: immunofluorescence was performed on cell culture or cryosections for the carotid artery. Proteins were visualized by using either secondary antibodies directly conjugated to Texas Red or the biotin/streptavidin-Texas Red conjugated amplification method (Amersham). Antibodies to SERCA 2a and 2b were previously described. Anti-PCNA (proliferating nuclear antigen) was from Abcam (UK), a-GFP and a-NFATc1 (K-18) were from Santa-Cruz. Nuclei were stained with Hoechst. Images were collected with a Zeiss LSM-510 confocal scanning laser microscope equipped with a 25 mW Argon laser and a 1 mW Helium-Neon laser, using a Plan Apochromat 63× objective (NA 1.40, oil immersion). Green fluorescence was observed with a 505-550 nm band-pass emission filter under 488 nm laser illumination and red fluorescence was observed with a 560 long-pass emission filter under 543 nm laser illumination. Pinholes are set at 1.0 Airy unit. Stacks of images were collected every 0.4 µm along the z-axis. Hoescht detection is done using the HBO mercury lamp (50 W) and a set filter 01 (excitation BP 365/12, beamsplitter FT 395, emission LP 397). All settings were kept constant for comparison. For double immunofluorescence, dual excitation using the multitrack mode (images taken sequentially), was achieve using the Argon and He/Ne lasers respectively.

Intracellular [Ca2+]i measurements: Cells were loaded with 4 µmol/L Fura 2 (Molecular Probes) and continuously superfused with control or test solutions at 37° C. using a PTR 200 perfusion temperature regulator (ALA Scientific Instruments, Westbury, N.Y., USA). The control solution contained (mmol/L): NaCl, 116; KCL, 5.6; CaCl$_2$, 1.8; MgCl$_2$, 1.2; NaHCO3, 5; NaH2PO4, 1; HEPES, 20; pH 7.3. Caffeine (10 mmol/L), ATP (1, 10 and 100 µmol/L) or 2,5-di-(t-butyl)-1,4-benzo-hydroquinone (tBHQ, 50 µmol/L) were used in the test solution. The excitation light was supplied by a high pressure 100 W xenon arc lamp and the 340 and 380 nm wavelengths selected by a monochromator (Cairn Research Ltd, Faversham, Kent, UK). Fluorescence images were collected every 2 seconds by a Sensicam QE CCD camera (PCO Computer Optics GmbH, Kelheim, Germany), digitized, and integrated in real time by an image processor (Metafluor, Princeton, N.J., USA). 340 and 380 background fluorescence signals were collected at the same rate and subsequently subtracted from respective fluorescent images. Results (ΔF/F) were expressed as ratios between 340 and 380 fluorescence signals measured during a response divided by the ratio measured in resting conditions, i.e. before the addition of an agent.

DNA binding assay: Electromobility shift assay was performed using 0.5 ng of $^{32}$P-labelled double-stranded NFAT probe (NFATc gel shift oligonucleotide, Santa Cruz, sc-2577) and 15 µg of nuclear extracts. Reaction mixtures were subjected to electrophoresis on a 5% polyacrylamide gel in non-denaturing conditions.

Example 6

We evaluated the effect of SERCA2a gene transfer on blood vessels in rats after balloon injury. We found that, compared to controls, SERCA2a gene transfer can prevent formation of a neointima.

Methods.

Balloon injury. After the left external carotid artery was exposed and heparin (35 IU) was administered intraperiotoneally, a 2Fr Fogarty embolectomy catheter (Baxter Healthcare Corp) was introduced into an external carotid arteriotomy incision, advanced to the common carotid artery, and inflated at 2 atmosphere and withdrawn 3 times with rotation. The catheter was then removed, and a dwelling catheter was introduced into the arteriotomy site. After both the proximal common carotid artery and the proximal internal carotid artery were clamped, viral infusion mixtures with 1×10$^9$ pfu of virus containing either SERCA2a or βgal diluted to a total volume of 100 µL was instilled via the arterial segment between the 2 clamps, and the external carotid artery was then ligated. Perfusion was restored in the common carotid artery after 30 minutes of instillation, and the neck incision was closed using 3-0 silk sutures.

Histochemical analysis. The animals were sacrificed after 7 and 14 days. Both the right and left common carotids were dissected and included in frozen specimen embedding solution. Transversal cryosections were performed on the middle portion of the artery and longitudinal sections on the proximal and distal portions. Hematoxylin-eosin staining was performed and the surface of lumen as well as the thickness of the media and intima were measured on at least 3-5 sections for different portions of the arteries. Expression of SERCA 2a was analysed by immunofluorescence using a rabbit antiS2a antibody followed by and anti-rabbit-TRITC secondary antibody.

Four groups were considered: 1) Non injured, non infected corresponding to the right carotids, 2) Injured, non-infected corresponding to the left carotid were no GFP labelling could be detected, 3) Injured, infected with β-Gal and 4) injured infected with S2a. The left carotids included in those two groups displayed clear GFP labelling on unfixed sections.

Results and Discussion

Figure 4:
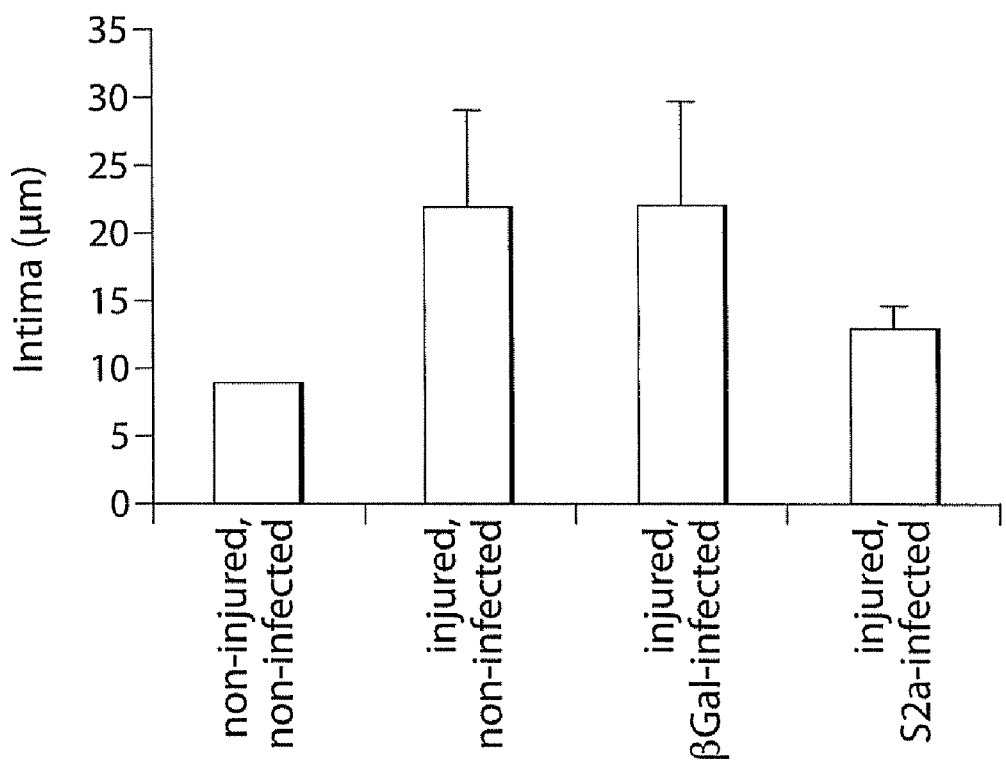
FIG. 4 provides a histogram showing the intima thickness under various conditions.

As shown in Table 2, there was no difference in the lumen area or in the media thickness between groups. There was a tendency to the prevention of intimal thickening with S2a gene transfer but due to the small number of animals this was not significant (FIG. 4).

TABLE 2

Morphometric measurements.

| | Lumen area (mm$^2$) | Media µm | Intima µm |
|---|---|---|---|
| Non injured, non-infected (n = 10) | 1.46 ± 0.085 | 47.3 ± 4.67 | 8.46 ± 0.22 |
| Injured, non-infected (n = 4) | 1.73 ± 0.114 | 41.26 ± 3.9 | 21.94 ± 7.28 |
| Injured, infected β-Gal (n = 4) | 1.95 ± 0.1 | 45.54 ± 2.7 | 21.89 ± 7.7 |
| Injured, infected S2a (n = 6) | 1.8 ± 0.23 | 45 ± 4.95 | 12.7 ± 1.82 |

We evaluated expression of the S2a in control and infected arteries. Expression of S2a is visualized in red by confocal imaging on 0.8 µm optical slices using a 63× oil immersion objective. In green is the auto-fluorescence of the elastin. The image were obtained using the multitrack mode with a He/Ne laser (ex: 543 nm-Em LP 560 nm) for the red fluorescence and with a Argon laser (Ex: 488 nm-Em: bp 505-550) for the green fluorescence. DIC represents the same image in differential interferential contrast.

A high level of S2a was observed in the media of the control carotid. When the vessel is injured, the smooth muscle cells from the media start to proliferate and to migrate to the neointima. We found that low level of S2a is observed in those cells, as seen in vitro. Infection with β-gal adenovirus did not prevent proliferation but restoration of a high level of S2a clearly inhibits the formation of the neointima. The differential interferential contrast image shows the adventitia which is not labelled with a-S2a indicating the absence of background.

We claim:

1. A method of reducing restenosis or stenosis in a subject comprising administering to an injured blood vessel, vein or artery of the subject a nucleic acid sequence that encodes a SERCA2a polypeptide, wherein the nucleic acid sequence is in a viral vector, thereby reducing the restenosis or stenosis.

2. The method of claim 1, wherein the restenosis is due to angioplasty, balloon angioplasty, insertion of a prosthesis, insertion of a graft, insertion of a stent, catheterization, or arterial blockage evaluation.

3. The method of claim 1, wherein the vector is an adenoviral or adeno-associated viral vector.

4. The method of claim 2, wherein the stenosis is due to insertion of a graft.

5. The method of claim 1, wherein the nucleic acid sequence encoding SERCA2a is operably linked to a promoter.

6. The method of claim 5, wherein the promoter is an inducible promoter.

7. The method of claim 3, wherein the vector is an adeno-associated vector.

8. The method of claim 1, wherein administration is by direct administration or indirect administration.

9. The method of claim 8, wherein direct administration if via injection or infusion.

10. The method of claim 1, wherein reduction in proliferation of vascular smooth muscle cells (VSMC) is achieved.

* * * * *